United States Patent
Murray et al.

(10) Patent No.: US 9,494,446 B2
(45) Date of Patent: Nov. 15, 2016

(54) TREADMILL PROVIDING GAIT ANALYSIS

(71) Applicant: DYACO INTERNATIONAL INC., Taipei (TW)

(72) Inventors: Brian Murray, Taipei (TW); Mao-Ying Huang, Taipei (TW); Hao Chiang, Taipei (TW)

(73) Assignee: DYACO INTERNATIONAL INC., Taipei (TW)

( * ) Notice: Subject to any disclaimer, the term of this patent is extended or adjusted under 35 U.S.C. 154(b) by 0 days.

(21) Appl. No.: 14/207,124

(22) Filed: Mar. 12, 2014

(65) Prior Publication Data

US 2015/0174444 A1 Jun. 25, 2015

(30) Foreign Application Priority Data

Dec. 20, 2013 (TW) .............................. 102147449 A

(51) Int. Cl.
- A63B 23/04 (2006.01)
- G01C 22/00 (2006.01)
- A63B 22/02 (2006.01)
- A61B 5/11 (2006.01)
- A63B 71/06 (2006.01)

(52) U.S. Cl.
CPC ............... *G01C 22/00* (2013.01); *A61B 5/112* (2013.01); *A63B 22/0235* (2013.01); *A63B 2071/0652* (2013.01); *A63B 2220/17* (2013.01); *A63B 2220/22* (2013.01); *A63B 2220/89* (2013.01)

(58) Field of Classification Search
CPC ........... A63B 24/0062; A63B 22/02–22/0292; A63B 2071/0652; A63B 2220/89; A63B 2220/22; A63B 2220/17; A61B 5/112; G01C 22/00
See application file for complete search history.

(56) References Cited

U.S. PATENT DOCUMENTS

| | | | | |
|---|---|---|---|---|
| 5,474,087 A | * | 12/1995 | Nashner ............... | A61B 5/1036 482/54 |
| 7,914,420 B2 | * | 3/2011 | Daly ................... | A63B 22/0235 119/700 |
| 2003/0153287 A1 | * | 8/2003 | Kuiri ............................ | 455/127 |
| 2003/0163287 A1 | * | 8/2003 | Vock .................... | A43B 3/0005 702/187 |
| 2008/0234107 A1 | | 9/2008 | Cox et al. | |
| 2009/0023556 A1 | | 1/2009 | Daly et al. | |
| 2012/0266648 A1 | | 10/2012 | Berme et al. | |

FOREIGN PATENT DOCUMENTS

| CN | 1965756 A | 5/2007 |
|---|---|---|
| TW | M289071 | 4/2006 |
| TW | M398939 | 3/2011 |

OTHER PUBLICATIONS

Kodesh, Einat et al. "Walking Speed, Unilateral Leg Loading, and Step Symmetry in Young Adults." *Gait & Posture.* vol. 35, 2012. pp. 66-69.

* cited by examiner

*Primary Examiner* — Loan T Thanh
*Assistant Examiner* — Rae Fischer
(74) *Attorney, Agent, or Firm* — Huffman Law Group, PC

(57) ABSTRACT

A treadmill is capable of performing a gait analysis and comprises a conveyor belt, a supporting plate, a driving mechanism, and at least two sensing assemblies. The conveyor belt is used for a user to walk or run in place. The driving mechanism drives the conveyor belt to run. The supporting plate supports the conveyor belt. The two sensing assemblies are fixed with the supporting plate, for respectively sensing the user's left and right heel strike. A left and right pulse diagram thus can be obtained from the sensing assemblies, and the gait analysis is performed according to the left and right pulse diagram.

6 Claims, 6 Drawing Sheets

TREADMILL PROVIDING GAIT ANALYSIS

CROSS-REFERENCE TO RELATED APPLICATIONS

The entire contents of Taiwan Patent Application No. 102147449, filed on Dec. 20, 2013, from which this application claims priority, are incorporated herein by reference.

BACKGROUND OF THE INVENTION

1. Field of the Invention

The present invention relates to exercise devices, and more particularly relates to an exercise device providing symmetry index.

2. Description of Related Art

Nowadays, people tend to lack adequate exercise due to busy lifestyles. To the extent running has become popular as a simple and effective means for squeezing physical activity into a tight schedule, it is not always practicable.

Gait analysis is the biomechanics systematic study of human motion, using instrument to measure and analyze walk movements. The gait analysis can be used to assess individuals with conditions affecting their ability to walk. Commercial treadmills typically have no gait analysis function. Recently, someone develop a treadmill employing a pressure plate or a force plate to perform gait analysis for the user.

SUMMARY OF THE INVENTION

In one general aspect, the present invention relates to exercise devices, and more particularly relates to a treadmill providing gait analysis.

In an embodiment of the present invention, a treadmill capable of performing a gait analysis is provided. The treadmill comprises a conveyor belt, a supporting plate, a driving mechanism, and at least two sensing assemblies. The conveyor belt is used for a user to walk or run in place. The driving mechanism drives the conveyor belt to run. The supporting plate supports the conveyor belt. The two sensing assemblies are fixed with the supporting plate, for respectively sensing the user's left and right heel strike. A left and right pulse diagram thus can be obtained from the sensing assemblies, and the gait analysis is performed according to the left and right pulse diagram.

Accordingly, the present invention provides a treadmill capable of performing a gait analysis, which can assess individuals with conditions affecting their ability to walk or the conditions of recovery.

DETAILED DESCRIPTION OF THE PREFERRED EMBODIMENT

Reference will now be made in detail to those specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations and components are not described in detail in order not to unnecessarily obscure the present invention. While drawings are illustrated in detail, it is appreciated that the quantity of the disclosed components may be greater or less than that disclosed, except where expressly restricting the amount of the components. Wherever possible, the same or similar reference numbers are used in drawings and the description to refer to the same or like parts.

Figure 1A:
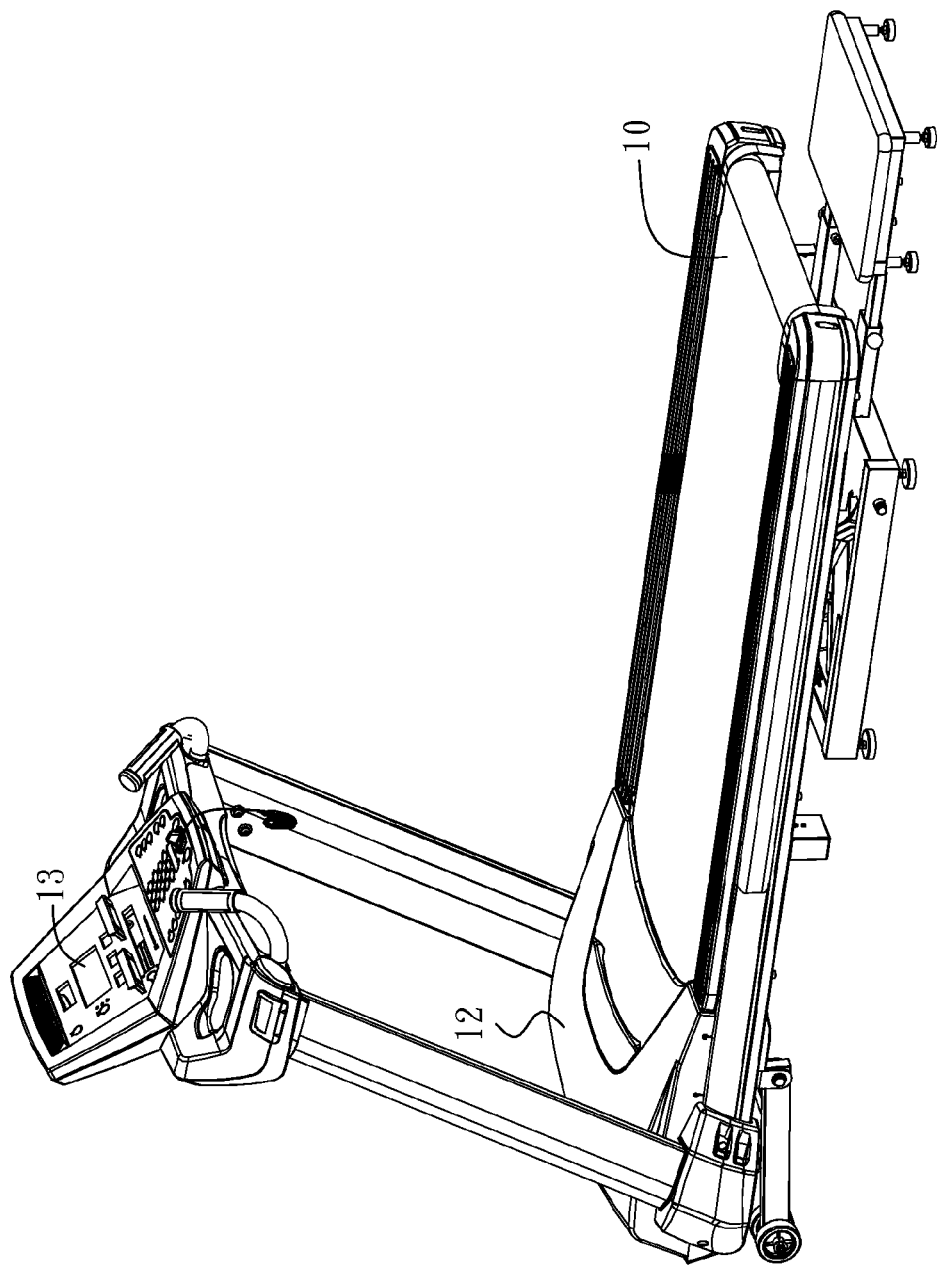
FIGS. 1A and 1B are perspective view and top view showing a treadmill capable of performing a gait analysis according to a preferred embodiment of the present invention.
Figure 1B:
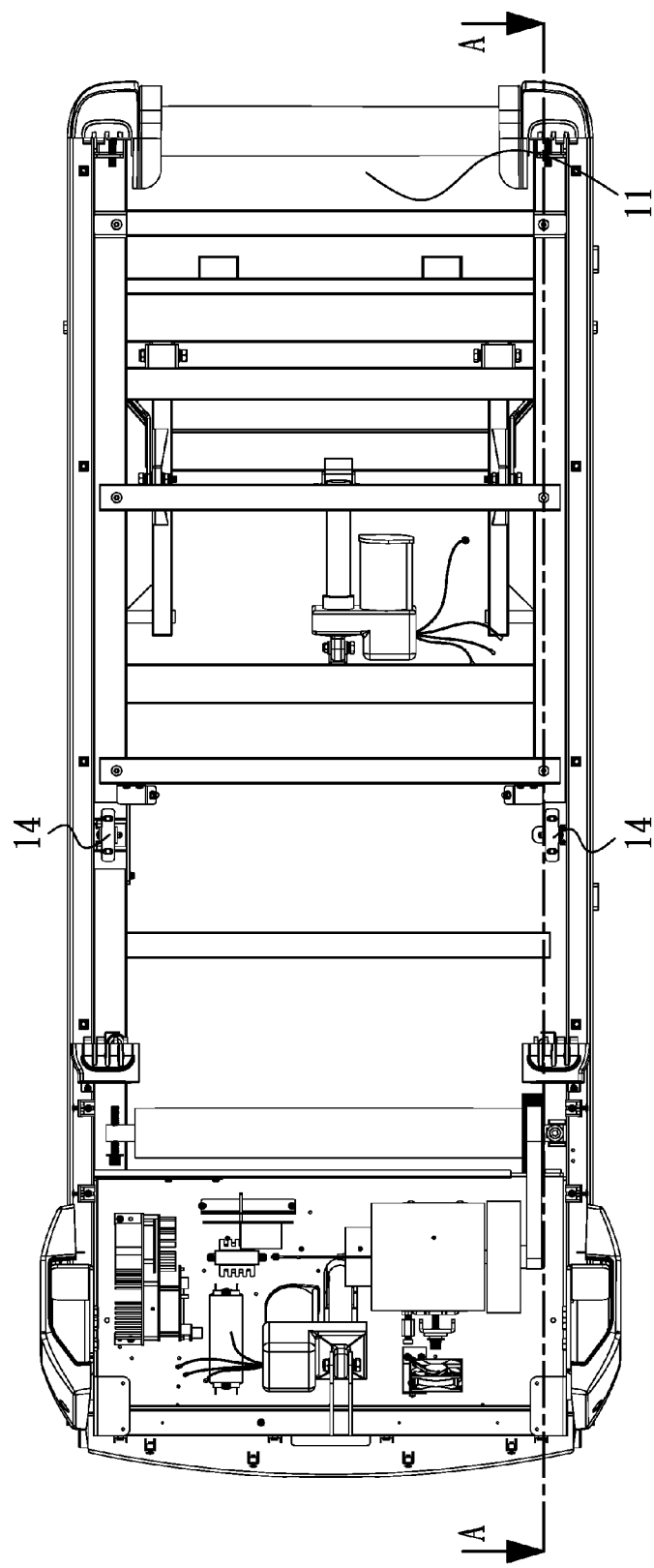

FIGS. 1A and 1B are perspective view and top view showing a treadmill 1 capable of performing a gait analysis according to a preferred embodiment of the present invention, in which some components are omitted from FIG. 1B for clearly showing essential components of the treadmill.

As shown in FIGS. 1A and 1B, the treadmill may comprise a conveyor belt 10, a supporting plate 11, a driving mechanism 12, a control panel 13, and at least two sensing assemblies 14. The conveyor belt 10 is used for a user to walk or run in place. The supporting plate 11 is arranged below the conveyor belt 10 for supporting the conveyor belt 10. The driving mechanism 12 drives the conveyor belt 10 to run. The two sensing assemblies 14 are fixed with the supporting plate 11, for respectively sensing the user's left and right heel strike. A left and right pulse diagram thus can be obtained from the sensing assemblies 14, and the gait analysis is performed according to the left and right pulse diagram. The detail is described as follows.

Figure 2:
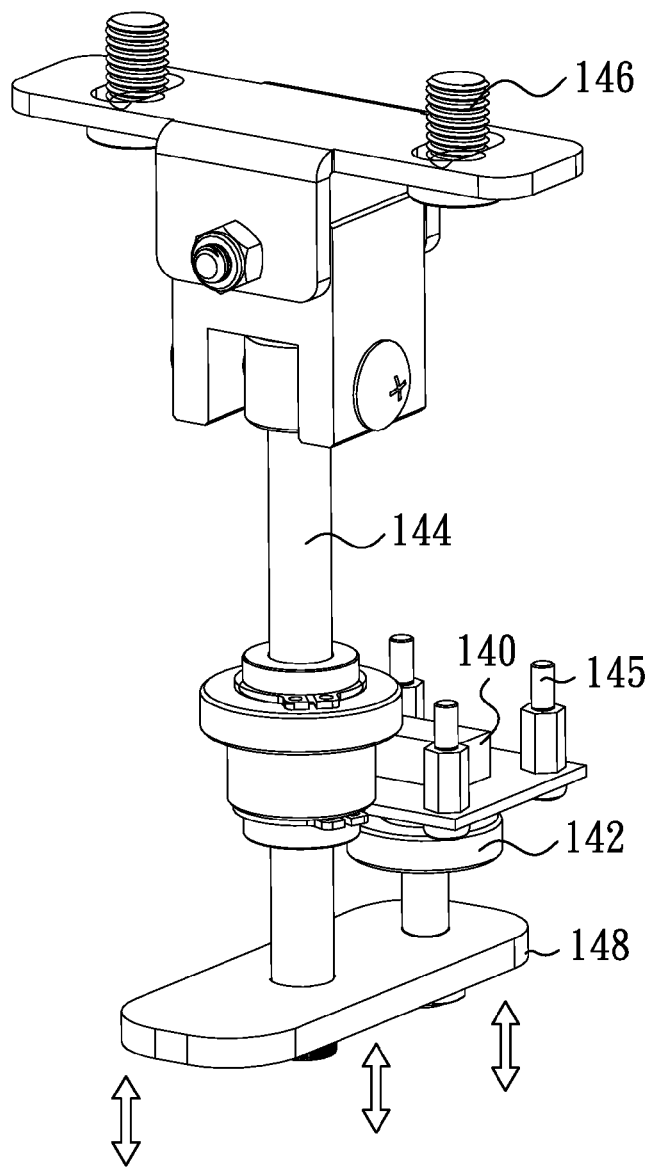
FIG. 2 shows the detail of the sensing assembly of the treadmill according to a preferred embodiment of the present invention.
Figure 5:
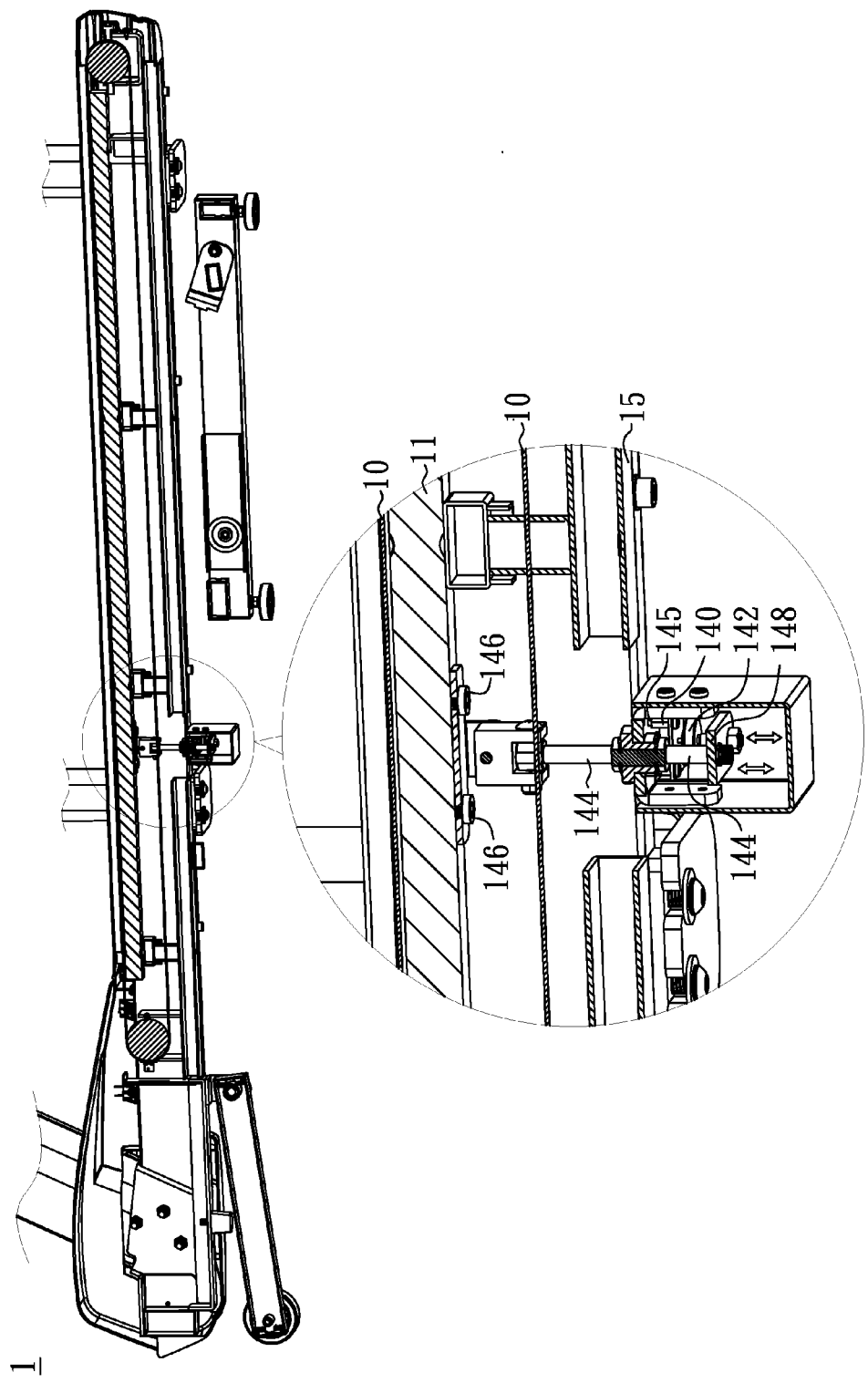
FIG. 5 is a cross-sectional view taken along line A-A of FIG. 1B.

FIG. 2 shows the detail of the sensing assembly 14 of the treadmill according to the preferred embodiment of the present invention. FIG. 5 is a cross-sectional view taken along line A-A of FIG. 1B. The two sensing assemblies 14 are respectively arranged near a left side and a right side of the supporting plate 11. Each sensing assembly 14 comprises a hall sensor 140, a magnet 142, a coupling member 144, and a fixing member 146. The sensing assembly 14 couples with the supporting plate 11 via the fixing member 146. The fixing member 146 may be, but is not limited to, a screw. Each Hall sensor 140 is a well-known transducer that varies its output voltage in response to a magnetic field. The hall sensor 140 does not fix with the coupling member 144, but fix with another mechanism. For example, the hall sensor 140 can fix with a mechanism 15 via several second fixing members 145 as shown in FIG. 2 and FIG. 5. The magnet 142 fixes with the coupling member 144. For example, a lower end of the coupling member 144 may have a flat portion 148, and the magnet 142 fixes with the flat portion 148 of the coupling member 144. When the user walks or runs, the coupling member 144 will vibrate with the supporting plate 11 but the hall sensor 140 remain static. The running or walking of the user hence causes vertical movements of the coupling member 144 and the magnet 142. The distance between the magnet 142 and the hall sensor 140 and the magnetic field to the hall sensor 140 are thus varied, and the hall sensor 140 outputs induction voltages depending on the distance between the magnet 142 and the hall sensor 140, so that the left and right pulse diagram can be obtained.

Figure 3:
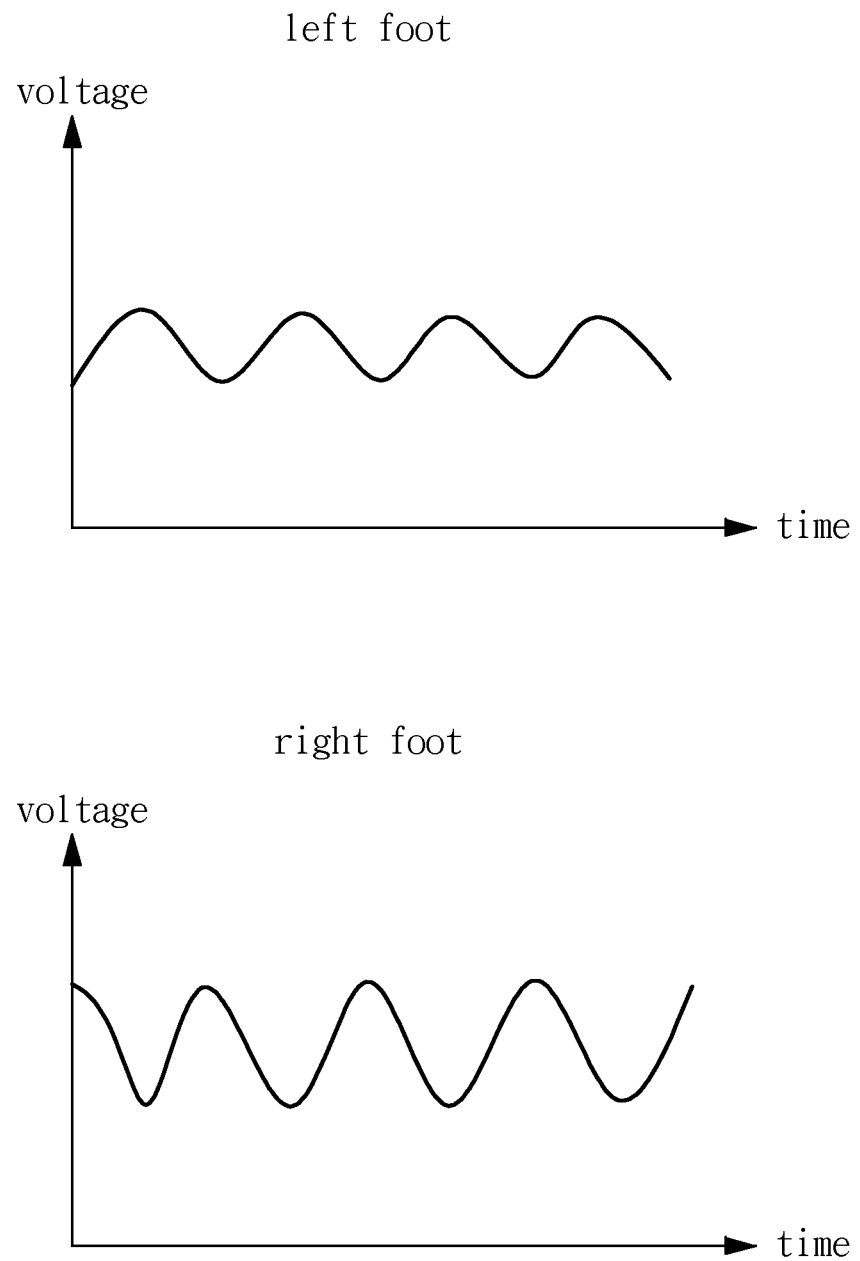
FIG. 3 shows a left and a right pulse diagram obtained from the sensing assemblies of the treadmill according to a preferred embodiment of the present invention.

FIG. 3 illustrates a left and a right pulse diagram obtained from the sensing assemblies of the treadmill according to a preferred embodiment of the present invention.

The left and right pulse diagram provide information regarding the relationship between the location of left foot (for instance, the tiptoe or heel portion of the left foot) and the time, and the relationship between the location of right foot (for instance, the tiptoe or heel portion of the right foot) and the time. By doing some computation, the gait analysis can be obtained.

In one embodiment, the gait analysis comprises a step number and/or a step frequency of the left and right foot of the user that walks or runs on the conveyor belt 10.

In one embodiment, the gait analysis comprises a step length of the left and right foot of the user that walks or runs on the conveyor belt 10.

Figure 4:
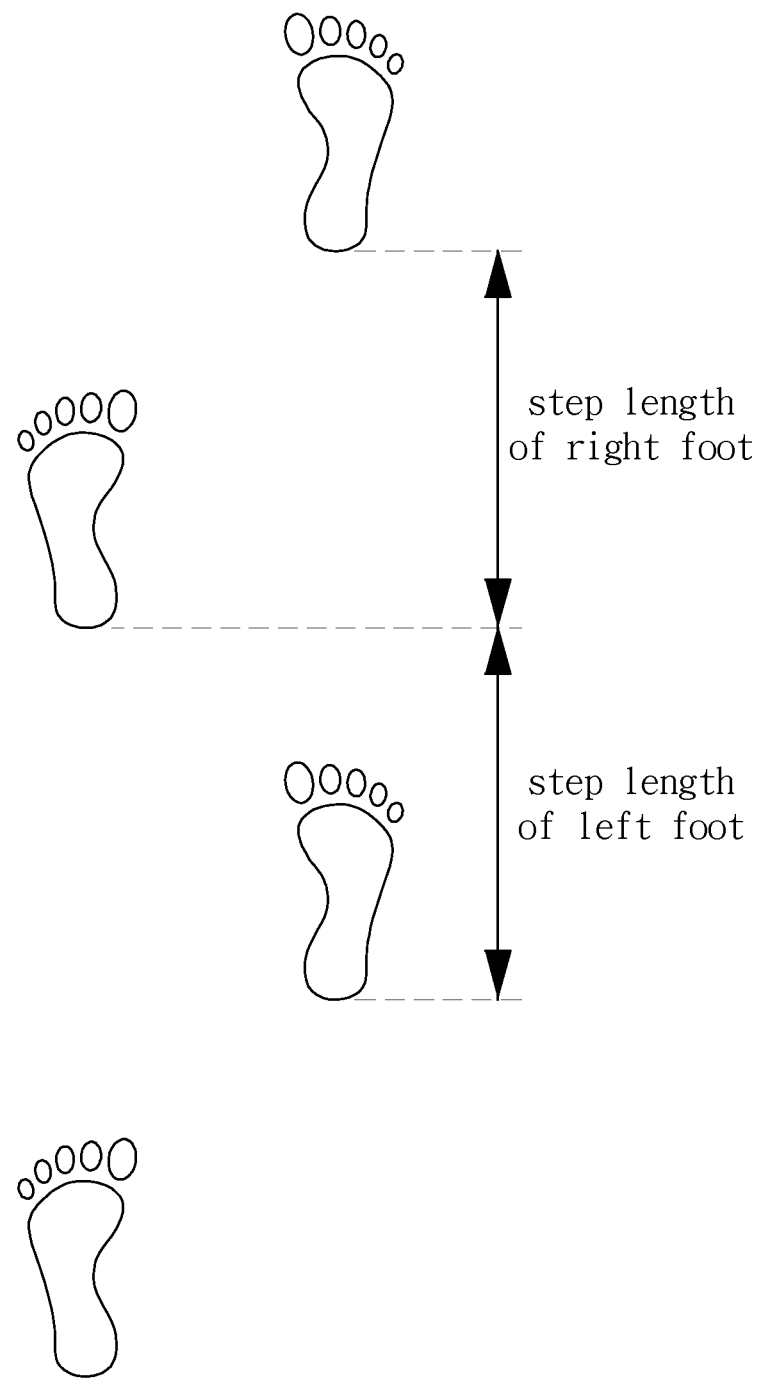
FIG. 4 illustrates the definition of step length according to a preferred embodiment of the present invention.

FIG. 4 illustrates the definition of step length according to a preferred embodiment of the present invention. As shown in FIG. 4, the step length of right foot is the distance between the right heel and the left heel in a pair of steps, and the step length of left foot is the distance between the left heel and the right heel in a pair of steps. Instead of heel-to-heel, the step length can be computed by other portions of the left and right foot, such as tiptoe-to-tiptoe.

In one embodiment, the gait analysis comprises a step length symmetry index, which is computed by the following formula:

$$(\text{step length symmetry index}) = \frac{2 \times |S_L - S_R|}{(S_L + S_R)} \times 100\%,$$

wherein $S_L$ denotes the step length of the left foot, and $S_R$ denotes the step length of the right foot.

An analysis module (not shown) can be used to execute the foregoing computations. The computed gait analysis results can be shown in the control panel 13.

Except the treadmill shown in FIGS. 1A and 1B, the sensing assemblies 14 can be used in other exercise devices for performing the gait analysis.

Accordingly, the present invention provides a treadmill capable of performing a gait analysis, which can assess individuals with conditions affecting their ability to walk or the conditions of recovery.

The intent accompanying this disclosure is to have each/all embodiments construed in conjunction with the knowledge of one skilled in the art to cover all modifications, variations, combinations, permutations, omissions, substitutions, alternatives, and equivalents of the embodiments, to the extent not mutually exclusive, as may fall within the spirit and scope of the invention. Corresponding or related structure and methods disclosed or referenced herein, and/or in any and all co-pending, abandoned or patented application(s) by any of the named inventor(s) or assignee(s) of this application and invention, are incorporated herein by reference in their entireties, wherein such incorporation includes corresponding or related structure (and modifications thereof) which may be, in whole or in part, (i) operable and/or constructed with, (ii) modified by one skilled in the art to be operable and/or constructed with, and/or (iii) implemented/made/used with or in combination with, any part(s) of the present invention according to this disclosure, that of the application and references cited therein, and the knowledge and judgment of one skilled in the art.

Conditional language, such as, among others, "can," "could," "might," or "may," unless specifically stated otherwise, or otherwise understood within the context as used, is generally intended to convey that embodiments include, and in other interpretations do not include, certain features, elements and/or steps. Thus, such conditional language is not generally intended to imply that features, elements and/or steps are in any way required for one or more embodiments, or interpretations thereof, or that one or more embodiments necessarily include logic for deciding, with or without user input or prompting, whether these features, elements and/or steps are included or are to be performed in any particular embodiment.

Although specific embodiments have been illustrated and described, it will be appreciated by those skilled in the art that various modifications may be made without departing from the scope of the present invention, which is intended to be limited solely by the appended claims.

What is claimed is:

1. A treadmill, comprising:

a conveyor belt on which a user walks or runs in place;

a supporting plate, arranged below the conveyor belt for supporting the conveyor belt;

a driving mechanism driving the conveyor belt to run; and a left sensing assembly and a right sensing assembly being fixed with a left side and a right side of the supporting plate, respectively, each of the left sensing assembly and the right sensing assembly comprising:

a Hall sensor fixing with a mechanism of the treadmill;

a coupling member being arranged below the supporting plate and fixing with the supporting plate, the running or walking of the user causing vertical movements of the coupling member; and a magnet fixing with the coupling member and being arranged toward the Hall sensor, the running or walking of the user causing vertical movements of the magnet; and wherein the hall sensor continually outputs an induction voltage in response to a magnetic field depending on a distance between the magnet and the Hall sensor, and wherein a left pulse diagram and a right pulse diagram plotted by a variation of voltage versus time are respectively obtained by the left sensing assembly and the right sensing assembly while the user runs or walks, allowing a gait analysis to be performed according to the left pulse diagram and the right pulse diagram.

2. The treadmill as set forth in claim 1, wherein the gait analysis comprises a step number of the left and right foot of the user that walks or runs on the conveyor belt.

3. The treadmill as set forth in claim 1, wherein the gait analysis comprises a step frequency of the left and right foot of the user that walks or runs on the conveyor belt.

4. The treadmill as set forth in claim 1, wherein the gait analysis comprises a step length of the left and right foot of the user that walks or runs on the conveyor belt.

5. The treadmill as set forth in claim 1, wherein the gait analysis comprises a step length symmetry index, which is computed by the following formula:

$$\text{(step length symmetry index)} = \frac{2 \times |S_L - S_R|}{(S_L + S_R)} \times 100\%,$$

wherein $S_L$ denotes the step length of the left foot, and $S_R$ denotes the step length of the right foot.

6. The treadmill as set forth in claim 1, further comprising a control panel for displaying the gait analysis.

\* \* \* \* \*